United States Patent [19]

Frost et al.

[11] Patent Number: 5,212,181
[45] Date of Patent: May 18, 1993

[54] 1-(3,4-DIHYDRO-2-OXO-1H-QUINOLIN-6-YL)-2-[4-(2-PHENYLETHYL)PIPERIDIN-1-YL]ETHANOL AND TO 1-(3,4-DIHYDRO-2-OXO-1H-QUINOLIN-6-YL)-2-[4-(2-PHENYLETHYL)PIPERIDIN-1-YL]ETHANONE, TO THEIR PREPARATION AND TO THEIR THERAPEUTIC APPLICATION

[75] Inventors: Jonathan Frost, Wissous; Patrick Lardenois, Bourg-la-Reine, both of France

[73] Assignee: Synthelabo, Paris, France

[21] Appl. No.: 777,176

[22] Filed: Oct. 16, 1991

[30] Foreign Application Priority Data

Oct. 18, 1990 [FR] France .................. 90 12872

[51] Int. Cl.⁵ .................... A61K 31/47; C07D 401/02
[52] U.S. Cl. .................... 514/312; 546/158
[58] Field of Search .................. 546/158; 514/312

[56] References Cited
U.S. PATENT DOCUMENTS 5,034,401 7/1991 Frost et al. .................. 514/323

*Primary Examiner*—C. Warren Ivy
*Assistant Examiner*—James H. Turnipseed
*Attorney, Agent, or Firm*—Wegner, Cantor, Mueller & Player

[57] ABSTRACT

A compound which is an ethanol or ethanone derivative of general formula (I)

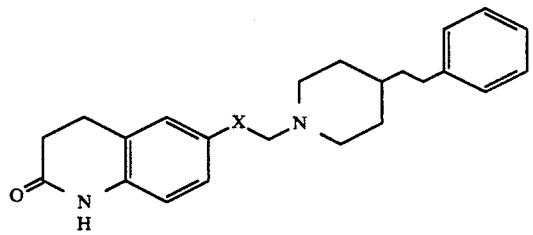

in which X represents CO or CHOH, or is an addition salt thereof with an acid, and, when X represents CHOH, is in the form of a pure enantiomer or a mixture of enantiomers, can be used for the treatment and prevention of cerebral disorders.

7 Claims, No Drawings

1-(3,4-DIHYDRO-2-OXO-1H-QUINOLIN-6-YL)-2-[4-(2-PHENYLETHYL)PIPERIDIN-1-YL]ETHANOL AND TO 1-(3,4-DIHYDRO-2-OXO-1H-QUINOLIN-6-YL)-2-[4-(2-PHENYLETHYL)PIPERIDIN-1-YL]ETHANONE, TO THEIR PREPARATION AND TO THEIR THERAPEUTIC APPLICATION

The present invention relates to 1-(3,4-dihydro-2-oxo-1H-quinolin-6-yl)-2-[4-(2-phenylethyl)piperidin-1-yl]ethanol and to 1-(3,4-dihydro-2-oxo-1H-quinolin-6-yl)-2-[4-(2-phenylethyl)piperidin-1-yl]ethanone, to their preparation and to their therapeutic application.

GB 2071094 discloses a general chemical formula which can represent numerous compounds, and in particular may represent the compounds of the present invention. However, GB 2071094 does not specifically disclose the latter or, for that matter, any analogous derivative comprising a [4-(2-phenylethyl)piperidin-1-yl] group. The compounds of the invention are therefore considered to be novel.

Moreover, GB 2071094 describes a number of therapeutic uses for the compounds disclosed therein but does not disclose the use of the compounds of the present invention.

The present invention provides a compound which is an ethanol or ethanone derivative of general formula (I)

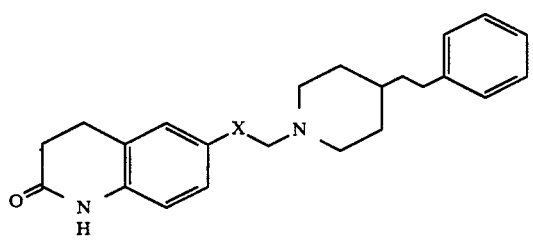

in which X represents CO or CHOH, or is an addition salt thereof with an acid, and, when X represents CHOH, is in the form of a pure enantiomer or a mixture of enantiomers.

Examples of compounds of general formula (I) include:

(±)-1-(3,4-dihydro-2-oxo-1H-quinolin-6-yl)-2-[4-(2-phenylethyl)piperidin-1-yl]ethanol; its hydrochloride or its methanesulfonate;

(−)-1-(3,4-dihydro-2-oxo-1H-quinolin-6-yl)-2-[4-(2-phenylethyl)piperidin-1-yl]ethanol;

(+)-1-(3,4-dihydro-2-oxo-1H-quinolin-6-yl)-2-[4-(2-phenylethyl)piperidin-1-yl]ethanol; and 1-(3,4-dihydro-2-oxo-1H-quinolin-6-yl)-2-[4-(2-phenylethyl)piperidin-1-yl]ethanone.

The present invention also provides a process for th preparation of compounds of general formula (I) which process comprises reacting 6-(2-chloro-1-oxoethyl)-3,4-dihydro-1H-quinolin-2-one with 4-(2-phenylethyl)-piperidine optionally in the form of an addition salt with an acid, in order to obtain the ethanone derivative of general formula (I) wherein X represents CO, and then, if desired, reducing the ethanone derivative to the ethanol derivative of general formula (I) wherein X represents CHOH, and if desired converting the derivative of formula (I) into an acid addition salt in a manner known per se.

The compounds of the invention may be obtained by reacting 6-(2-chloro-1-oxoethyl)-3,4-dihydro-1H-quinolin-2-one (described in GB 2071094) with 4-(2-phenylethyl)-piperidine (described in Chemical Abstracts, vol. 52, 8138a (1958)). The ketone of general formula (I), where X represents CO, is first obtained, which optionally may not be isolated, before reducing it to an alcohol of general formula (I), where X represents CHOH, for example by means of a reducing agent such as potassium borohydride. The racemic alcohol thus obtained may be resolved in a known manner, for example by fractional crystallization of the diastereoisomer addition salts obtained with a chiral acid, and release of the base.

The following examples illustrate the preparation of the compounds according to the invention. Elemental microanalyses and IR and NMR spectra confirm the structures of the products obtained.

EXAMPLE 1

(±)-1-(3,4-Dihydro-2-oxo-1H-quinolin-6-yl)-2-[4-(2-phenylethyl)piperidin-1-yl]ethanol 3.35 g (15 mmol) of 6-(2-chloro-1-oxoethyl)-3,4-dihydro-1H-quinolin-2-one, 3.38 g (15 mmol) of 4-(2-phenylethyl)piperidine hydrochloride, 3 g ($\approx$30 mmol) of sodium carbonate, 80 ml of ethanol and 20 ml of water are introduced into a round-bottomed flask placed under nitrogen.

The mixture is refluxed for 45 min, cooled, 7 g of potassium borohydride are added and the mixture is stirred for 4 h.

150 ml of water are added, the mixture is again stirred for 30 min, the precipitate filtered, washed with water, spun and dried, producing 4.1 g of product. The product is purified by silica gel column chromatography, eluting with a 9/1 mixture of dichloromethane/methanol, and then recrystallised in ethanol.

3.55 g of pure product are finally obtained.

Melting point: 164–165° C.

EXAMPLE 2

(±)-1-(3,4-Dihydro-2-oxo-1H-quinolin-6-yl)-2-[4-(2-phenylethyl)piperidin-1-yl]ethanol, its hydrochloride and its methanesulphonate.

22.3 g (100 mmol) of 6-(2-chloro-1-oxoethyl)-3,4-dihydro-1H-quinolin-2-one, 22.5 g (100 mmol) of 4-(2-phenylethyl)piperidine hydrochloride, 20 g ($\approx$200 mmol) of sodium carbonate, 450 ml of ethanol and 150 ml of water are introduced into a round-bottomed flask placed under nitrogen.

The mixture is refluxed for 1 h, cooled, the precipitate (the ketone of general formula (I)) is separated by filtration and 6.9 g thereof are removed for subsequent purification.

The remaining precipitate is reintroduced into the reaction medium, 40 g of potassium borohydride are added and the mixture is stirred at room temperature for 15 h. The mixture is poured into 900 ml of water, stirred for 30 min, the precipitate is separated by filtration, washed with water, dried and recrystallised in 600 ml of ethanol. 24 g of compound are finally obtained.

Melting point: 163–164.5° C.

In order to prepare the hydrochloride, 10 g (26.4 mmol) of the free base are dissolved in 400 ml of propan-2-ol under reflux and a stream of gaseous hydrochloric acid is bubbled into the solution. After cooling on an ice bath, the precipitate is separated by filtration, recrystallised in 350 ml of propan-2-ol containing 1% concentrated hydrochloric acid and dried in the presence of phosphorus pentoxide.

6.92 g of the hydrochloride are finally obtained.

Melting point: 189–190° C.

In order to prepare the methanesulphonate, 10 g (26.4 mmol) of the free base are dissolved in 400 ml of propan-2-ol under reflux, filtered while hot and a solution of 2.7 g (28 mmol) of methanesulphonic acid in 10 ml of propan-2-ol is added to the filtrate. After cooling on an ice bath, the precipitate is filtered, recrystallised in 200 ml of ethanol and dried in the presence of phosphorus pentoxide.

8.63 g of the methanesulphonate are finally obtained.

Melting point: 197–198° C.

EXAMPLE 3

1-(3,4-Dihydro-2-oxo-1H-quinolin-6-yl)-2-[4-(2-phenylethyl)piperidin-1-yl]ethanone 6.9 g of the intermediate ketone previously separated as in EXAMPLE 2 are recrystallised in 130 ml of propanol, the crystals are washed with ethanol and dried. 5.56 g of compound are obtained.

Melting point: 182–183° C.

EXAMPLE 4

(−)-1-(3,4-Dihydro-2-oxo-1H-quinolin-6-yl)-2-[4-(2-phenylethyl)piperidin-1-yl]ethanol 20 g (52.8 mmol) of (±)-1-(3,4-dihydro-2-oxo-1H-quinolin-6-yl)-2-[4-(2-phenylethyl)piperidin-1-yl]ethanol, 8 g (52.8 mmol) of L(+)-mandelic acid and 100 ml of ethanol are introduced into an Erlenmeyer flask and the mixture, which collects into a mass, is stirred. The mixture is refluxed while adding 1100 ml of ethanol (dissolution of the salt), the solution is filtered while hot, the filtrate is reheated until the salt is again dissolved, and the solution is allowed to cool at room temperature for 4 h without stirring.

The precipitate is separated by filtration, washed with a small amount of ethanol, dried, and recrystallised twice in ethanol. 7.21 g of salt are obtained.

Melting point: 216–216.5° C.

7.0 g of the salt are removed and treated with ammonium hydroxide in dichloromethane in order to release the base therefrom. After separation of the organic phase and evaporation of the solvent, the residue is recrystallised in 90 ml of propanol.

4.64 g of laevorotatory enantiomer are finally obtained.

Melting point: 184.5–185° C. $[\alpha]_D^{20} = -45.4$ (c=1; CHCl$_3$).

EXAMPLE 5

(+)-1-(3,4-Dihydro-2-oxo-1H-quinolin-6-yl)-2-[4-(2-phenylethyl)piperidin-1-yl]ethanol The mother liquors obtained from the preceding fractional crystallization are evaporated and the residue is treated with ammonium hydroxide in dichloromethane. After separation of the organic phase and evaporation of the solvent, 14.15 g (37.3 mmol) of base are obtained which are suspended in 100 ml of ethanol, 5.68 g (37.3 mmol) of D(−)-mandelic acid are added and the mixture is refluxed while adding 1100 ml of ethanol (dissolution of the salt). The solution is filtered while hot and the filtrate is allowed to cool at room temperature for 4 h without stirring.

The precipitate is separated by filtration and recrystallised twice in ethanol. 6.1 g of salt are obtained.

Melting point: 216–217° C.

6.0 g of the salt are removed and treated with ammonium hydroxide in dichloromethane to release the base. After separation of the organic phase and evaporation of the solvent, the residue is recrystallised in 70 ml of propanol.

3.97 g of dextrorotatory enantiomer are finally obtained.

Melting point: 185–185.5° C. $[\alpha]^{20} = +43.3°$ (c=1; CHCl$_3$).

The compounds of the invention have been the subject of pharmacological trials which have demonstrated their usefulness as active substances for medicinal products.

Thus, the neuroprotective activity of the compounds of the present invention has been shown in a focal ischemic model by ligature of the median cerebral artery in mice, according to a method analogous to that described in Brain Research, 522, (1990), 290–307.

Six days after occlusion of the median cerebral artery by electrocoagulation under halothane anaesthesia, the mice are again anaesthetized and the cerebral cortex ipsilateral to the occlusion is collected. After homogenization of the tissue, the extent of the cerebral infarct is evaluated by measuring the increase in the density of peripheral benzodiazepine sites ($\omega_3$) by means of the compound [$^3$H]-PK 11195 from New England Nuclear. The treatments are curatively administered by the intraperitoneal route at the following times: 5 min, 3 h, 6 h, 18 h and 24 h.

With the compounds of the invention, the reduction in the size of the lesion is of the order of 50 to 70 %, depending on the compound, at a dose of 10 mg/kg.

The compounds of the invention have also been the subject of an inhibition test for the binding of [$^3$H] ifenprodil to the sigma receptors of rat cerebral cortex (Schoemaker et al., Eur. J. Pharmacol., 183, 1670, (1990)).

The 150 to 230 g Sprague-Dawley male rat is sacrificed and the cerebral cortex is homogenised in 20 volumes of ice-cold 50 mM Tris-HCl buffer (pH =7.4 at 25° C.) by means of an Ultra-Turrax ™ (Ikawerk) or Polytron ™ (Kinematica) apparatus.

The homogenate is washed twice by centrifugation for 10 minutes at 45,000 ×g, the pellet being resuspended in fresh buffer. The final pellet is taken up in 20 volumes of the same buffer.

An aliquot of 100 μl of this suspension is incubated in a final volume of 1,000 μl with 0.5 nM of [$^3$H]ifenprodil (specific activity: 30 to 35 Ci/mmol) for 30 minutes at 37° C. in the absence or in the presence of a competing substance. After incubation, the membranes are recovered by filtration on Whatman GF/B ™ filters pretreated with 0.05 % polyethyleneimine, and then washed with two times 5 ml of ice-cold buffer.

The nonspecific binding with 10 μM ifenprodil is determined, the data are analyzed by the usual methods and the IC$_{50}$ concentration is calculated, that is, the concentration which inhibits the binding of [$^3$H]ifenprodil by 50 %.

The IC$_{50}$ values for the compounds of the invention are, in this test, between 3 and 50 nM.

The compositions of the invention have been furthermore the subject of an inhibition test of the binding of [$^3$H]ifenprodil to receptors sensitive to rat cerebral cortex polyamines, following the procedure described by Shoemaker et al., Eur. J. Pharmacol., 176, 249-250, (1990).

The 150 to 230 g Sprague-Dawley male rat is sacrificed and the cerebral cortex is homogenised in 20 volumes of ice-cold 50 mM Tris-HCl buffer (pH=7.4 at 0° C.) by means of an Ultra-Turrax TM (Ikawerk) or Polytron TM (Kinematica) apparatus.

The homogenate is washed twice by centrifugation for 10 minutes at 45,000 ×g, the pellet being resuspended in fresh buffer. The final pellet is taken up in 20 volumes of the same buffer.

An aliquot of 100 μl of this suspension is incubated in a final volume of 1,000 μl with 1 nM of [$^3$H]ifenprodil (specific activity: 30 to 35 Ci/mmol) for 120 min at 0° C., in the presence of 3 μM of GBR 12909 (Research Biochemicals Inc., Natick, MA, USA), in the absence or in the presence of a competing substance.

After incubation, the mixture is diluted with 5 ml of ice-cold 50 mM Tris-HCl buffer (pH =7.4 at 0° C.) and the membranes are recovered by filtration on Whatman GF/B TM filters pretreated with 0.05 % polyethyleneimine, and then washed with two times 5 ml of ice-cold buffer. The nonspecific binding with 10 μM ifenprodil is determined, the data are analyzed by the usual methods and the IC$_{50}$ concentration is calculated, that is, the concentration which inhibits the binding of [$^3$H]ifenprodil by 50 %.

The IC$_{50}$ values for the compounds of the invention are, in this test, between 6 and 16 nM.

Finally, the compounds of the invention have been studied with respect to their effects on maximum convulsions induced in mice by supramaximum electroshock. The procedure for this test is described by E. A. Swinyard and J. H. Woodhead in Antiepileptic Drugs, Raven Press, New York, 111-126 (1982).

30 minutes after intraperitoneal administration of the test compound, the number of mice having convulsions (extension of the hind legs) is noted immediately after application of an electrical current (0.4 s, 60 mA, 50 Hz) by means of transcorneal electrodes. The results are expressed as AD$_{50}$, the dose which protects 50 % of the animals, calculated according to the method of J. T. Lichtfield and F. Wilcoxon (J. Pharm. Exp. Ther., 96, 99-113 (1949)) from 3 or 4 doses, each administered to a group of 8 to 10 mice.

The AD$_{50}$ values of the compounds of the invention are, in this test, between 10 and 40 mg/kg by the intraperitoneal route.

Other tests carried out in vivo on mice have moreover shown that the compounds according to the invention have anticonvulsant properties towards the effects of N-methyl-D-aspartate (NMDA).

The results of tests carried out on the compounds of the invention suggest that they may be used for the treatment and the prevention of cerebral disorders such a those which follow, for example, an ischemic attack, a cardiac or respiratory failure, a thrombosis or a cerebral embolism, for the treatment of cerebral senility, of dementia following multiple infarcts, of senile dementia, for example Alzheimer's disease or Pick's disease, for the treatment of olivo-ponto-cerebellar atrophy and other neurodegenerative diseases such as Huntington's chorea, for the treatment of schizophrenia, for the treatment of cranial or spinal traumatisms, for the treatment of convulsive states, for the treatment of certain cancers, for the treatment of AIDS, and as antiemetic, for example during the treatment of cancers with cisplatinum.

The present invention also provides pharmaceutical compositions comprising as active ingredient a compound of general formula (I) or an addition salt thereof with an acid together with a pharmaceutically acceptable excipient.

To this effect, the compounds of the present invention may be provided in any pharmaceutical form suitable for enteral or parenteral administration, for example in the form of tablets, sugared pills, hard gelatine capsules, capsules, suppositories, solutions or suspensions for swallowing or for injecting, in doses which enable a daily administration of 1 to 1,000 mg of active substance.

We claim:

1. A compound which is an ethanol or ethanone derivative of general formula (I)

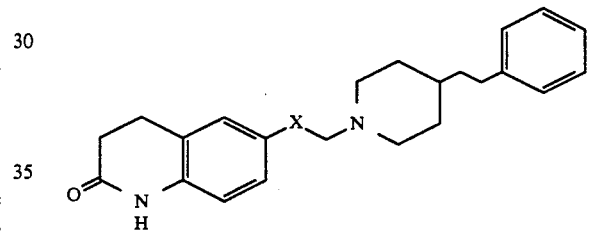

in which X represents CO or CHOH, or is an addition salt thereof with an acid, and, when X represents CHOH, is in the form of a pure enantiomer or a mixture of enantiomers.

2. (±)-1-(3,4-Dihydro-2-oxo-1H-quinolin-6-yl)-2-[4-(2-phenylethyl)piperidin-1-yl]ethanol, its hydrochloride or its methanesulfonate.

3. (−)-1-(3,4-Dihydro-2-oxo-1H-quinolin-6-yl)-2-[4-(2-phenylethyl)piperidin-1-yl]ethanol.

4. (+)-1-(3,4-Dihydro-2-oxo-1H-quinolin-6-yl)-2-[4-(2-phenylethyl)piperidin-1-yl]ethanol.

5. 1-(3,4-Dihydro-2-oxo-1H-quinolin-6-yl)-2-[4- (2-phenylethyl)piperidin-1-yl]ethanone.

6. A pharmaceutical composition comprising as active ingredient a compound as claimed in claim 1, together with a pharmaceutically acceptable excipient.

7. A method of treatment of cerebral disorders which comprises administering to a patient a compound as claimed in claim 1.

* * * * *